United States Patent [19]

Blanchette et al.

[11] Patent Number: 5,292,343
[45] Date of Patent: Mar. 8, 1994

[54] HAND SHAKE FOR IMPLANTED MEDICAL DEVICE TELEMETRY

[75] Inventors: Christine M. Blanchette, Maple Grove; James W. Busacker, Buffalo; David E. Dalluge; John J. Grevious, both of Minneapolis; Paul B. Wyborny, Coon Rapids; Glenn M. Roline, Anoka; Lucy M. Nichols, Maple Grove; David L. Thompson, Fridley, all of Minn.

[73] Assignee: Medtronic, Inc., Minneapolis, Minn.

[21] Appl. No.: 896,645

[22] Filed: Jun. 10, 1992

Related U.S. Application Data

[63] Continuation-in-part of Ser. No. 765,475, Sep. 25, 1991, Pat. No. 5,127,404, which is a continuation of Ser. No. 468,407, Jan. 22, 1990, abandoned.

[51] Int. Cl.⁵ .................................................. A61N 1/00
[52] U.S. Cl. .................................... 607/32; 128/903
[58] Field of Search ............ 128/419 PT, 422, 419 PS, 128/419 D, 419 PG, 419 P, 419 R, 903, 420.6; 340/573, 502–505; 371/2.1, 4; 607/32, 60

[56] References Cited

U.S. PATENT DOCUMENTS

| | | | |
|---|---|---|---|
| 4,066,086 | 1/1978 | Alferness et al. | 128/421 |
| 4,431,991 | 2/1984 | Bailey et al. | 375/5 |
| 4,432,360 | 2/1984 | Mumford et al. | 128/419 PG |
| 4,550,370 | 10/1985 | Baker | 364/413 |
| 4,556,063 | 12/1985 | Thompson et al. | 128/419 |
| 4,561,443 | 12/1985 | Hogrefe et al. | 128/903 |
| 4,606,047 | 8/1986 | Wilkinson | 375/102 |
| 4,616,223 | 10/1986 | Naaijer | 340/825.36 |
| 4,675,656 | 6/1987 | Narcisse | 128/903 |
| 4,814,751 | 3/1989 | Hawkins et al. | 340/573 |
| 4,947,407 | 8/1990 | Silivian | 128/419 R |
| 5,113,869 | 5/1992 | Nappaholy et al. | 128/903 |
| 5,127,404 | 7/1992 | Wyborny | 128/419 |
| 5,157,604 | 10/1992 | Axford et al. | 128/903 |

Primary Examiner—Lee S. Cohen
Assistant Examiner—Marianne Parker
Attorney, Agent, or Firm—Harold R. Patton

[57] ABSTRACT

A method of and apparatus for telemetering both analog and digital data transcutaneously between an implantable medical device and an external receiver, such as between an external programmer and an implantable cardiac pacer. A damped carrier at 175 kilohertz is pulse position modulated by digital data. The data, along with synchronization and identification codes, are positioned into predefined ranges within predefined frames as measured by individual time periods. The data is uniquely identified by the position of a burst of the carrier within the predefined range. An automatically initiated hand shake protocol maintains the link over slight variations in programmer head position with an indicator notifying the operator when repositioning is required. Analog data may be transferred in digital form or alternatively transferred using phase modulation of the carrier bursts. A cyclic redundancy code is used for link error detection.

3 Claims, 18 Drawing Sheets

HAND SHAKE FOR IMPLANTED MEDICAL DEVICE TELEMETRY

CROSS REFERENCE TO CO-PENDING APPLICATIONS

This application is a continuation-in-part of U.S. Appln. Ser. No. 07/765,475, filed Sep. 25, 1991, now U.S. Pat. No. 5,127,404 incorporated herein by reference, which is a continuation of U.S. Appln. Ser. No. 07/468,407, filed on Jan. 22, 1990, now abandoned.

BACKGROUND OF THE INVENTION

1. Field of the Invention

The present invention generally relates to implantable medical devices, and more particularly, pertains to telemetry for percutaneously transmitting analog and digital data between a programmer and an implantable medical device.

2. Description of the Prior Art

The earliest implantable medical devices were designed to operate in a single mode and with no direct percutaneous communication. Later it became clinically desirable to vary certain of the operating parameters and change modes of operation. This was accomplished through the use of programmers and other external devices which transferred commands percutaneously to the implanted medical device.

The communication between the implant and the external world was at first primarily indirect. The operation of an implantable cardiac pacer could be observed, for example, in the electrocardiogram of the patient. Soon it became known that data could be sent from the implanted cardiac pacer by modulating the stimulation pulses in some manner. This can only provide a low band pass channel, of course, without interfering with the clinical application of the device. Change of the pacing rate to indicate battery condition was a commonly used application of this technique.

As implantable cardiac pacers became more complex, the desirability to transfer more data at higher speeds resulted in the percutaneous transmission of data using a radio frequency carrier The data to be transmitted is of two basic types, namely, analog and digital. The analog information can include, for example, battery voltage, intracardiac electrocardiogram, sensor signals, output amplitude, output energy, output current, and lead impedance. The digital information can include, for example, statistics on performance, time markers, current values of programmable parameters, implant data, and patient and unit identifiers.

The earliest RF telemetry systems transmitted analog and digital information in separate formats, resulting in inefficient utilization of the available power/bandwidth. Also, these modulation schemes tended to be less than satisfactory in terms of battery consumption, and do not lend themselves to simultaneous transmission of differing data types.

Many types of RF telemetry systems are known to be used in connection with implantable medical devices, such as cardiac pacemakers. An example of a pulse interval modulation telemetry system used for transmitting analog and digital data, individually and serially, from an implanted pacemaker to a remote programmer is disclosed in U.S. Pat. No. 4,556,063 issued to Thompson et al., herein incorporated by reference. An example of a modern pacemaker programmer for use with programmable cardiac pacemakers having RF telemetric capabilities is disclosed in U.S. Pat. No. 4,550,370 issued to Baker, herein incorporated by reference. A major difficulty in the use of such prior art systems is the need to maintain the communication link using continuous activation of the reed switch. This tends to place the radio frequency components in a less than optimal physical orientation. In addition to the bandwidth limitations found by the differing analog and digital formats, considerable bandwidth of digital channels tends to be consumed for forward error detection. Oftentimes, in previous systems this was accomplished by completely redundant separate transmissions.

SUMMARY OF THE INVENTION

The present invention overcomes the disadvantages of the prior art systems by percutaneously transmitting both analog and digital data between the implantable medical device and the external device in a single format. This format provides for transmission of both data types while employing a hand shake protocol to maintain continuity of the link and while using cyclic redundancy coding to provide forward detection of link transmission errors.

The RF carrier is pulse position modulated with the digital data to conserve battery energy. In this manner, only a short burst of the carrier, e.g., one cycle, is actually needed to transmit a given unit of digital data. The time position of that burst relative to a synchronizing standard determines the value of the digital data unit transmitted.

To accomplish this pulse position modulation, a frame of about 2 milliseconds is defined. Within this frame are positioned a synchronizing burst, a frame identifier burst, and two data bursts. The synchronizing burst is positioned at a fixed position in every frame. The frame identifier and data positions are variable, such that the corresponding bursts occur within a range of time within the frame. The range in which a burst is found defines the nature or type of the variable. The position in the range defines the value of the variable.

The frame identifier burst defines the type of data to be found within the frame. One particular frame identifier defines a two frame couplet as a hand shake link maintenance verification. The hand shake request is made by the transmitting device at approximately 250 millisecond intervals. In response thereto, the receiving device must transmit a hand shake reply within the data range of that same frame. Upon receiving the hand shake reply, the transmitting device sends a unique hand shake confirmation within the second frame of the couplet.

Failure to successfully complete the hand shake protocol at a given 250 millisecond interval causes an indicator on the external RF head to be lit. This signifies that the operator must reposition to rf head to maintain operation of the link. If the RF head is not properly repositioned within five seconds (i.e. 20 unsuccessful hand shake attempts), the link is deemed to be broken and must be re-initiated before data can be transmitted.

The link is initiated by closing of the reed switch by a magnetic field sourced from the RF head. Because the hand shake protocol is used to maintain the link, the reed switch need not be closed during the entire data transmission. However, to ensure that devices made in accordance with the present invention are downward compatible, preferably, the link may be maintained by continuous closure of the reed switch during the entire transmission without regard to whether any hand shake attempts are successful.

Analog data may be transmitted in two ways in accordance with the present invention. The first technique is to convert the analog data into digital information. This digital information is used to pulse position modulate the burst of carrier energy in the same manner as other digital information.

A second technique for transmitting the analog information is to phase shift modulate the carrier bursts in response to the analog data. Because an ordinary frame lasting two milliseconds contains four bursts of 175 kilohertz energy, it is theoretically possible to transmit analog data with a pass band of up to one kilohertz. However, most of the analog signals of interest tend to have a much lower pass band. Therefore, the burst used to synchronize the frame for digital purposes is also used to transmit a constant phase standard. This means that only three bursts per frame are available for analog transmission lowering the theoretical pass band of the analog channel to 750 hertz. However, the constant transmission of the phase standard prevents the low frequency shifts associated with phase drift between the transmitting and receiving devices.

To reduce the pass band consumed in the forward error detection function, a cyclic redundancy code is transmitted along with the digital data. This code is computed to be the remainder bits after a polynomial using the transmitted data bits as coefficients, is divided by a generator polynomial. The receiving device divides the polynomial formed using the received data bits and cyclic redundancy code as coefficients. If the remainder is not zero, a transmission error has occurred and the transmitting device is notified that the subject data block must be retransmitted.

The cyclic redundancy function may be implemented in either software or hardware within the transmitting and receiving devices. However, for greatest efficiency, a given device should employ only one form. In the preferred embodiments, hardware implementation is utilized for both transmitting and receiving.

BRIEF DESCRIPTION OF THE DRAWINGS

Other objects of the present invention and many of the attendant advantages of the present invention will be readily appreciated as the same becomes better understood by reference to the detailed description when considered in connection with the accompanying drawings in which like reference numerals designate like parts throughout the figures thereof and wherein.

DETAILED DESCRIPTION OF THE PREFERRED EMBODIMENTS

Figure 1:
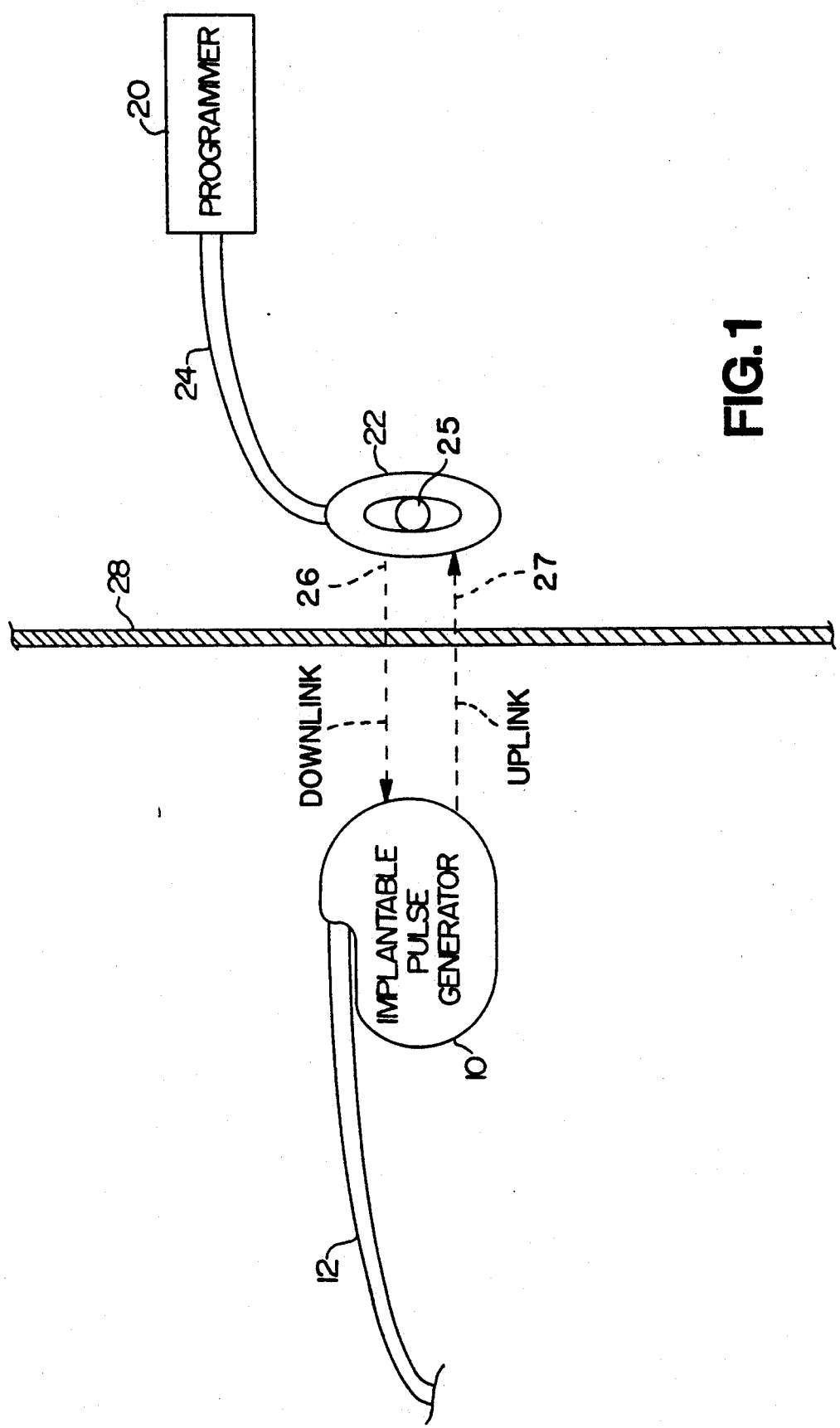
FIG. 1 is a simplified schematic view of an implantable medical device employing the improved telemetry format of the present invention.

FIG. 1 is a simplified schematic diagram of the present invention as employed in a communication link between an external programmer and an implanted cardiac pacer. An implantable pulse generation 10 is implanted in the patient under the outer skin barrier 28. Implantable pulse generator 10 is electrically coupled to the heart of the patient using at least one cardiac pacing lead 12 in a manner known in the art. Percutaneous telemetry data is transmitted from implantable pulse generator 10 by an RF up link 26 utilizing the improved telemetry format to a receiving antenna 22, which is coupled to a programmer 20 via a cable 24. Receiving antenna 22 also contains a magnet which activates a reed switch in implantable pulse generator 10 as a safety feature, as taught in U.S. Pat. No. 4,006,086 issued to Alferness et al., herein incorporated by reference. The telemetry data is demodulated and presented to the attending medical personnel by programmer 20.

Similarly, programmer 20 transmits signals via radio frequency energy sent from antenna 22 under control of signals transferred from programmer 20 along cable 24. This energy reaches implantable pulse generator 10 by down link 27. The transmitted signals are utilized by implantable pulse generator 10 after demodulation.

In accordance with the present invention, indicator 25 provides notification to the operator of the link that a disruption has occurred. In the preferred mode, indicator 25 is a light emitting diode, LED. The LED is illuminated whenever a periodically scheduled (i.e. approximately every 250 milliseconds) handshake has been unsuccessful. Upon seeing indicator 25 illuminated, the operator is instructed to reposition antenna 22 slightly to improve reception along the link. Failure to properly reposition antenna 22 for five seconds (i.e. 20 unsuccessful hand shake attempts) causes the link to be terminated. The operator is so notified by programmer 20 using standard techniques. The hand shake protocol is explained in more detail below.

Figure 2:
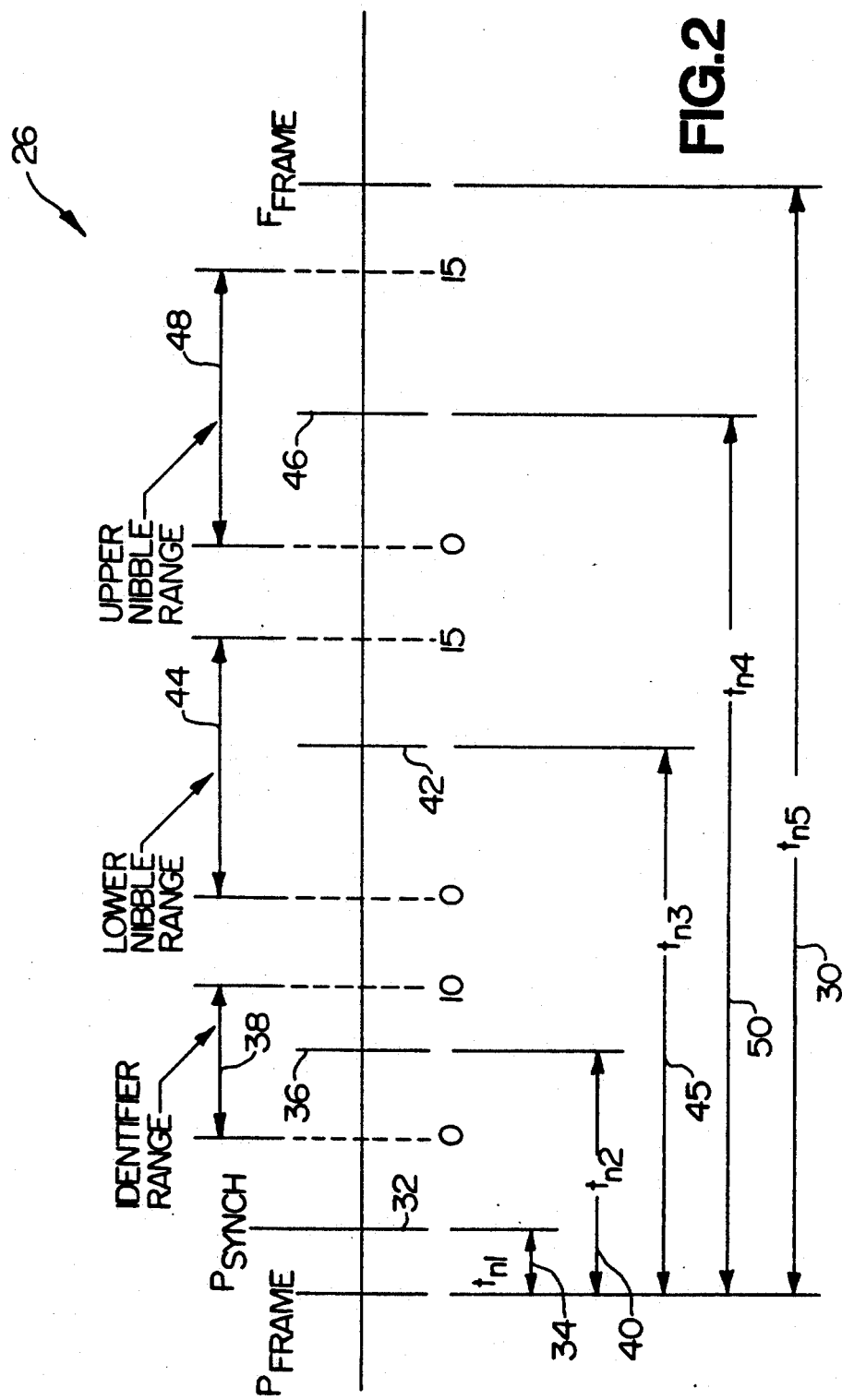
FIG. 2 is a Conceptual view of one frame of the improved telemetry format of the present invention.

FIG. 2 is a schematic diagram of the protocol utilized by RF up link 26. These links use a damped 175 kilohertz RF carrier which is phase shift modulated for analog data and pulse position modulated for digital (or digitized) data, as described in detail below. Shown at 30, the basic timing unit of the format is a frame, having a duration of $t_{n5}$. It will be understood by those skilled in the art, however, that the present invention can be practiced using fixed-length frames having periods of shorter or longer duration. In the preferred embodiment, the main timing source of implantable pulse generator 10 comprises a standard 32.768 kilohertz crystal clock which provides a basic clock cycle of 30.52 microseconds. Thus, a frame comprised of 64 clock cycles and extending over a fixed time interval of 1.953125 milliseconds a convenient frame period, since such frame period is a binary multiple of the basic clock cycle.

A unique synchronizing signal is positioned within a first fixed range of each frame 30. This signal comprises a synchronizing RF pulse 32 which is located a time $t_{n1}$ within frame 30. To properly function as a synchronizing pulse, it must be located at a fixed point within the first fixed range of frame 30, as shown at 34.

A four-bit frame identifier code is positioned within a second fixed range of each frame 30, such second fixed range comprising an identifier range 38. Identifier range 38 uses a total of eleven basic clock cycles as shown. This identifier code comprises an identifier RF pulse 36 which is pulse position modulated within the identifier range 38. The position of identifier pulse 36 within identifier range 38 identifies the nature or type of data found within each frame 30 which is being transmitted, such as peak sense, peak pressure, sense threshold and others, as described in further detail below. Shown at 40, time interval $t_{n2}$ thus uniquely represents the value of identifier pulse 36, which value in turn identifies the data type being transmitted within frame 30. As explained below, one unique frame identifier code is a hand shake request employed within the hand shake protocol to maintain the link communication.

Each frame 30 transfers one eight-bit byte of digital data along with the identifier code. This data is divided into two portions comprised of four bits of data each. A first portion of this data, namely the four least significant bits of the data byte, is positioned within a third fixed range of frame 30, such third fixed range comprising a lower nibble range 44. A second portion of this data, namely the four most significant bits of the data byte, is positioned within a fourth fixed range of frame 30, such fourth fixed range comprising an upper nibble range 48.

A lower nibble pulse 42 is pulse position modulated within lower nibble range 44, such that its value is uniquely identified by its location, such as at a time $t_{n3}$ shown at 45. An upper nibble pulse 46 is also pulse position modulated within upper nibble range 48, such that its value is uniquely identified by its location, such as at a time $t_{nr}$ shown at 50. Lower nibble range 44 and upper nibble range 48 each comprise sixteen basic clock cycles, permitting each of the sixteen unique values of the four-bit nibble to be specified. To prevent data overlap, suitable guard bands are positioned between each of the ranges within the frame to uniquely identify the synchronizing pulses, thereby avoiding undefined and erroneous data transmission.

As explained in more detail below, identifier pulse 36, lower nibble pulse 42, and upper nibble pulse 46 are phase shift modulated with analog data in addition to being pulse position modulated with digital information. The pulse position within the frame is used along with the instantaneous analog signal value to define the instantaneous phase of the carrier. Synchronizing RF pulse 32 has a fixed phase as well as a fixed pulse position such that it can conveniently serve as a phase standard for analog demodulation as well as a time standard for digital demodulation.

Figure 3:
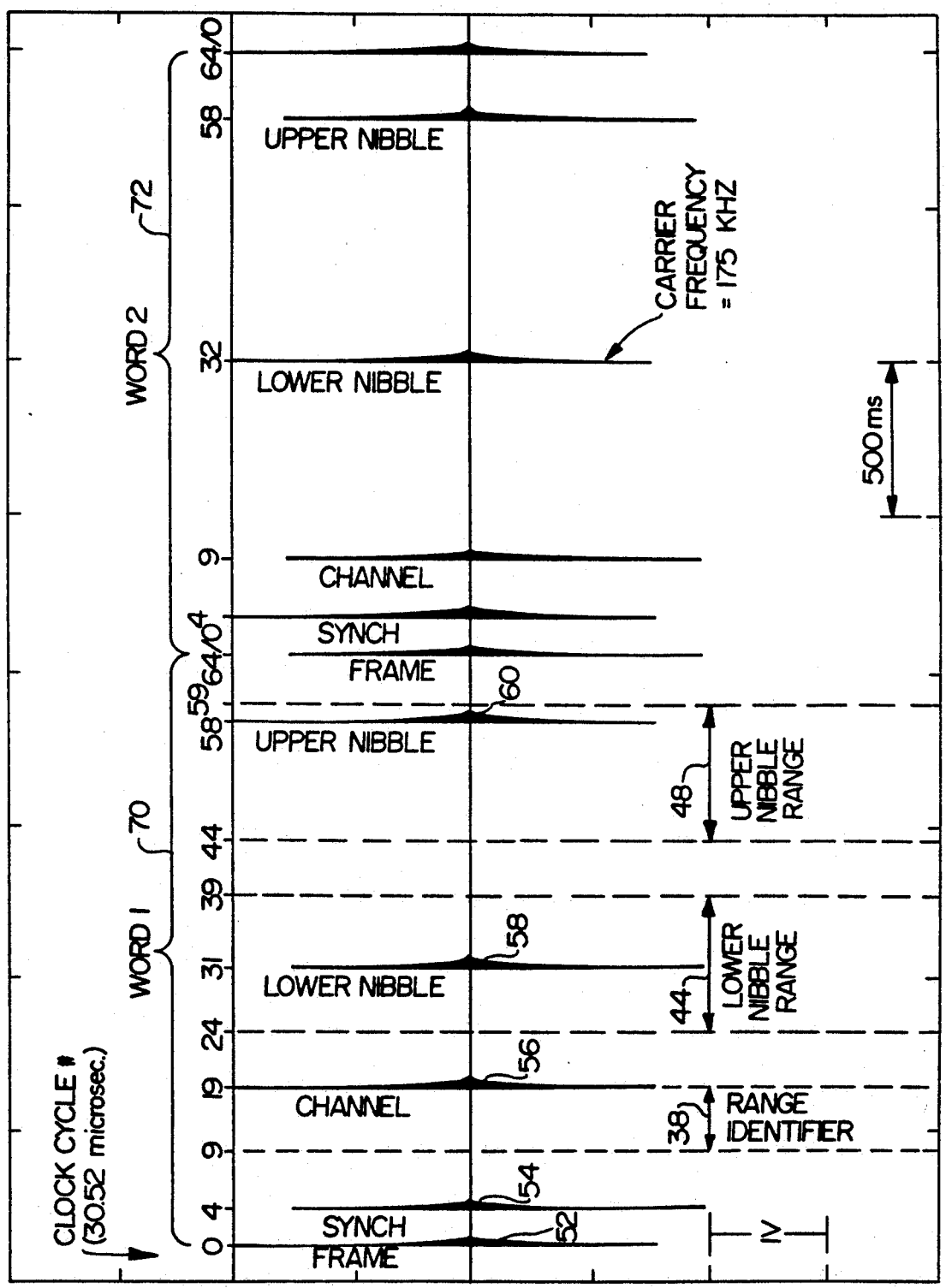
FIG. 3 is a view of the actual transmission pattern of two frames of the improved telemetry format.

FIG. 3 is a diagram of two frames of transmission from either RF up link 26 or down link 27, wherein a first frame corresponds to Word 1 shown at 70, and a second frame corresponds to Word 2 shown at 72. A count of clock cycles is indicated along an upper horizontal axis of this diagram for each frame. Each basic clock cycle has a duration of 30.52 microseconds. The first frame at 70 is initiated by an RF pulse 52. A synchronizing RF pulse 54 is shown uniquely identified as precisely four clock cycles later. Because the guard bands are all greater than four clock cycles, no combination of a frame identifier and data can appear as a synchronizing pulse. Synchronizing pulse 54 is used to provide frame synchronization between the transmitter and the receiver.

An identifier RF pulse 56 is located within identifier range 38, defined as nine to nineteen basic clock cycles from the beginning of frame 70. In Word 1, for example, identifier pulse 56 is located at clock cycle nineteen. For RF up link 26, this identifies the frame as a particular type of data transfer, namely, "Sense Threshold" as indicated in Table 1 below.

TABLE 1

| (Up link Frame Identifiers) | |
|---|---|
| Position | Identification |
| 9 | Memory |
| 10 | Hand shake request |
| 11 | EGM-1 |
| 12 | Markers |
| 13 | Peak Sense |
| 14 | Pressure Waveform |
| 15 | Peak dp/dt |
| 16 | Peak Pressure |
| 17 | Delta Capacitor Voltage |
| 18 | Activity Counts |
| 19 | Sense Threshold |

A lower nibble RF pulse 58 is located within lower nibble range 44, which range is defined as twenty-four to thirty-nine basic clock cycles from the beginning of frame 70. In Word 1, for example, lower nibble pulse 58 is located at clock cycle thirty-one, specifying a decimal value of seven on a scale of zero to fifteen. An upper nibble RF pulse 60 is located at clock cycle fifty-eight within upper nibble range 48, which range is defined as forty-four to fifty-nine basic clock cycles from the beginning of frame 70, and is demodulated in similar fashion.

Though not readily observable in FIG. 3, RF pulses 56, 58, and 60 can be phase shift modulated with analog data as well. RF pulses 52 and 54 have a constant phase and thus serve as a phase standard for analog demodulation.

Figure 4:
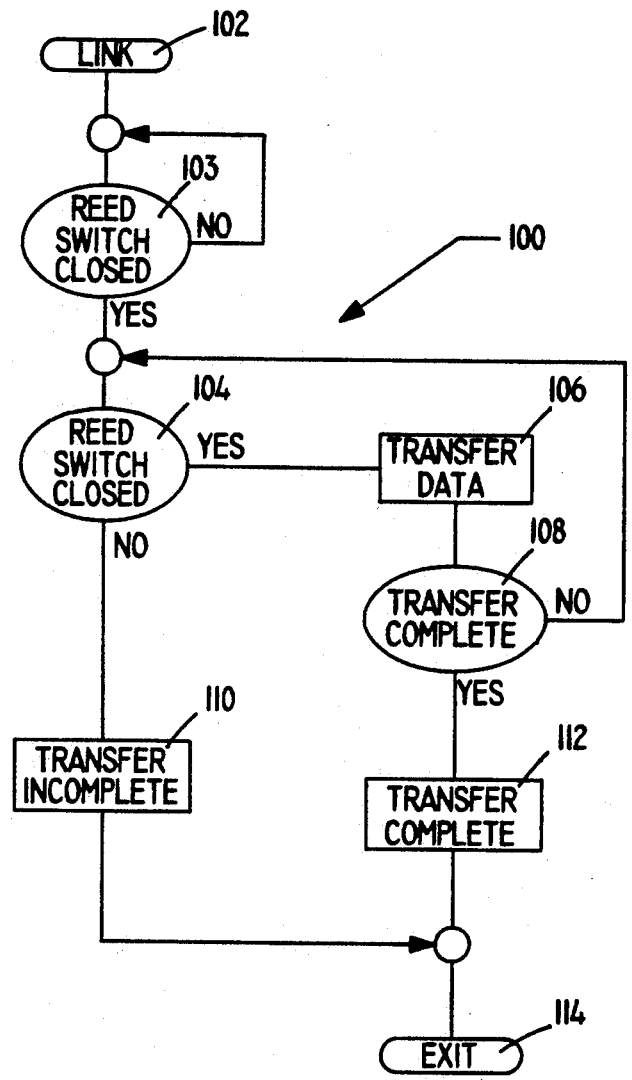
FIG. 4 is a flow chart of a prior art method of link management.

FIG. 4 is a flow chart 100 for the common prior art method of maintaining the transmission link. The basis of this technique is a magnet located within the housing of antenna 22 (see also FIG. 1). This housing is often called an RF head within the art. Presence of the magnetic field generated by this magnet closes a reed switch within implantable pulse generator 10 if in sufficiently close proximity. The hardware details of this approach are provided in the above identified and incorporated U.S. patent to Alferness et al.

Functionally, the technique is started at element 102. The RF head is manually positioned by the attending medical personnel at element 105. Element 103 determines whether the magnet within the RF head has in fact closed the reed switch within implantable pulse generator 10. If element 107 extinguishes the LED indicator, the operator is notified that the RF head position is satisfactory. As soon as the transfer is initiated at element 106 and until completion of the entire transfer as determined by element 108, element 104 permits further data transfer via element 112 as long as the reed switch within implantable pulse generator 10 remains closed. If the reed switch opens before the transfer is completed, element 110 records a failure to complete the transmission. If the transfer has been completed, however, as determined by element 108, element 114 provides a normal exit.

As can be appreciated from this approach, the reed switch must be closed and remain closed for the entire duration of the transmission to be deemed satisfactory. As data streams become longer, incomplete transfers become more prevalent because of patient movement, inadvertent movement of antenna 22, and other practical difficulties.

Figure 5:
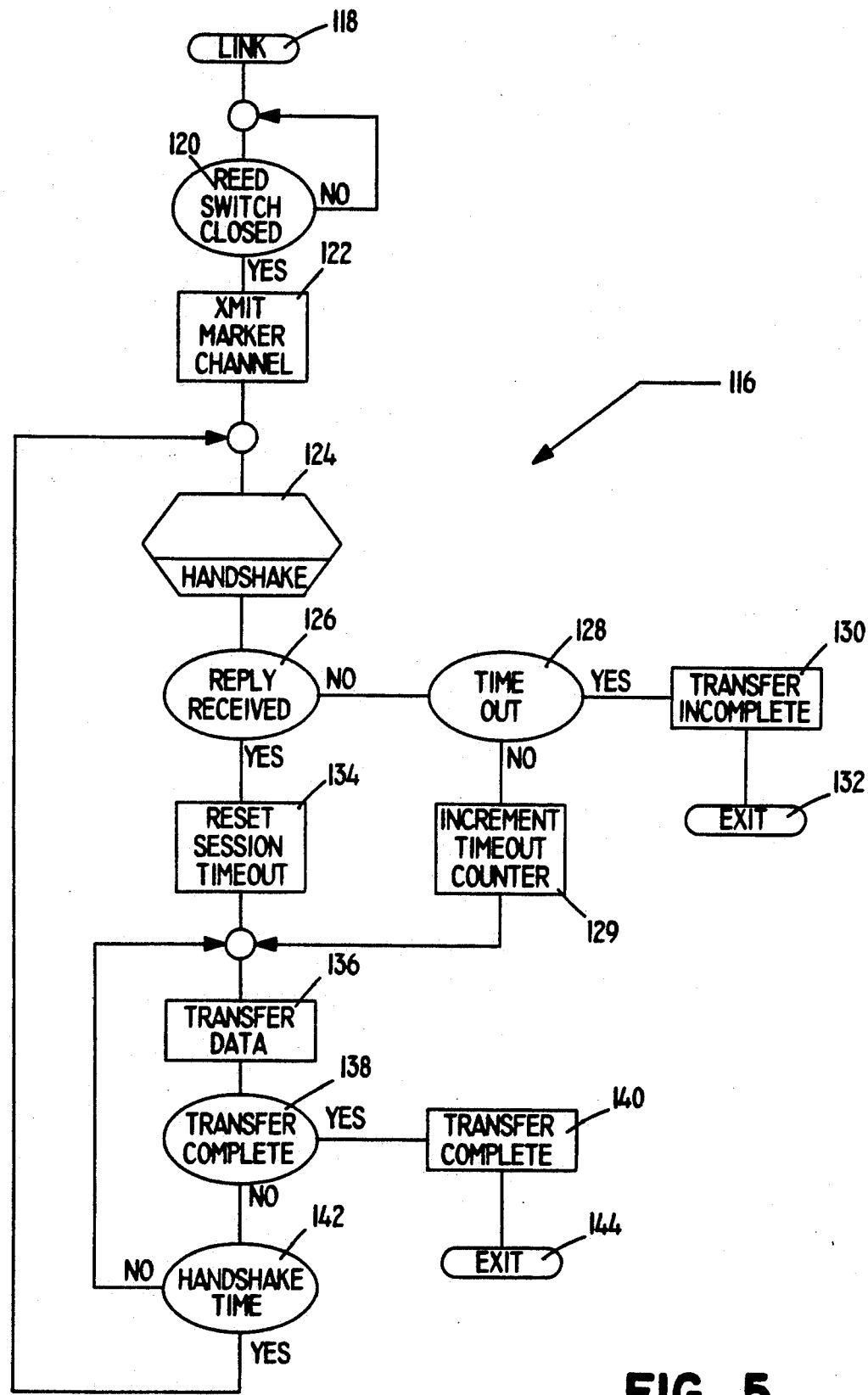
FIG. 5 is a flow chart showing link maintenance according to the present invention.

FIG. 5 is a flow chart 116 of the method of maintaining the link according to the preferred mode of the present invention. The link protocol is entered at element 118. As with the prior art approach (see also FIG. 4), the RF head is manually positioned at element 119 and checked by element 120, which causes initiation of the link upon the closing of the reed switch. However, unlike the prior art approach, the link may be maintained without continuous closing of the reed switch as will become apparent. Upon initiation of the link, element 122 causes implantable pulse generator 10 to commence sending the marker channel timing signals which are well known in the art to programmer 20.

The basic hand shake procedure is performed at element 124. This procedure is described in more detail below. If a reply was not received by the requesting device during the hand shake procedure, element 126 routes control to element 128 to determine whether a time out has occurred. Time out is defined as a five second period of time during which no hand shake procedure has been successful. In the preferred mode, the hand shake procedure is executed every 250 milliseconds, which means that time out corresponds to 20 consecutive unsuccessful hand shake procedures. If a time out has occurred, element 130 records an incomplete transfer and exit is obtained via element 132. If a time out has not occurred, element 129 increments the time out counter indicating that another unsuccessful consecutive hand shake procedure has been experienced and returns control to element 136 for data transfer.

Whenever element 126 determines that the hand shake procedure has been successful, element 134 rests the session time out timer. This corresponds to a break in the chain of unsuccessful hand shake procedures if any. After the reset, the link will not time out for at least five more seconds.

Data transfer occurs at element 136. Element 138 determines whether the current data transfer is complete. This may be defined within the data stream itself. If yes, element 140 records a successfully completed data transfer and exit occurs via element 144. If the entire data transfer is not yet complete, element 142 determines whether it is time for another hand shake procedure. A new hand shake procedure is scheduled every 250 milliseconds. The resultant time interval between hand shake procedures (requiring two frames) corresponds to 124 data frames which consume about 248 milliseconds.

If the 250 milliseconds has not yet elapsed, control is returned to element 136 for additional data transfer. If the 250 milliseconds has elapsed, however, control is given to element 124 to schedule another hand shake procedure. Thus it can be seen that the link can be maintained without continuous closure of the reed switch. By using forward error detection techniques along with retransmission of incorrect data blocks, as described below, the link can be efficiently maintained even though actual data transmission continuity is temporarily interrupted.

Figure 6:
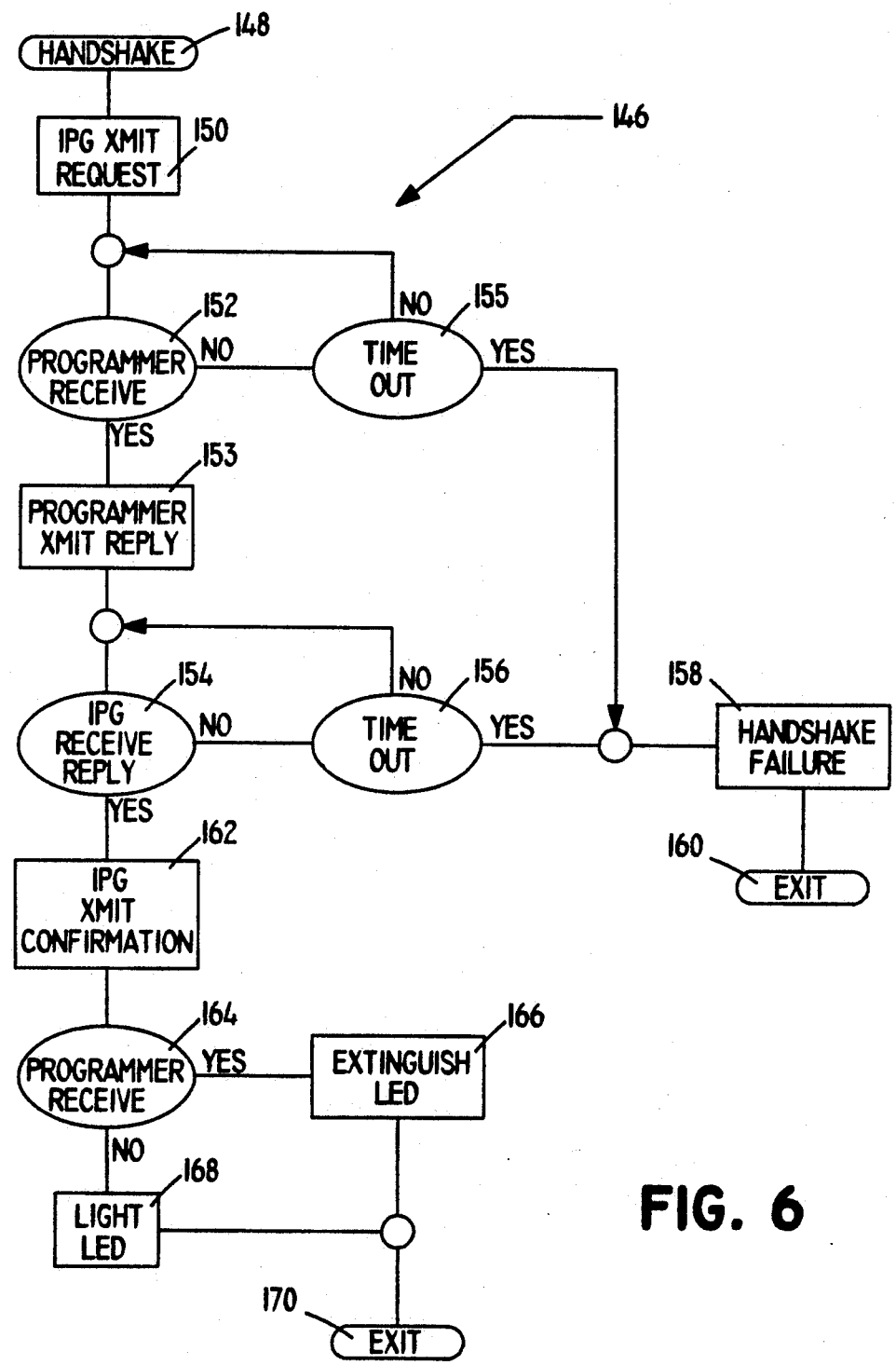
FIG. 6 is a flow chart of the basic hand shake procedure.

FIG. 6 is a flow chart 146 of the hand shake procedure. Upon being called, entry is via element 148. In the preferred mode, implantable pulse generator 10 transmits the hand shake request at element 150. However, those of skill in the art will readily appreciate that the hand shake request could also be transmitted from programmer 20. The transmitted hand shake request is a frame having a unique frame identifier (see above) without any data pulses (as shown below).

If programmer 20 does not receive the hand shake request as shown by element 152, control is given to element 155 to continue waiting until a time out has occurred. This time is on the order of tens of microseconds, because the hand shake reply must be positioned within the same frame as described in more detail below. After the time out, element 155 transfers control to element 158 to record a hand shake failure and exit the procedure at element 160.

If programmer 20 properly receives the hand shake request, it generates a reply pulse at element 153. Element 154 determines whether implantable pulse generator 10 has received the reply. Element 156 illustrates that some tens of microseconds are expended awaiting the reply. If none is received in time, element 158 records the hand shake failure and exits via element 160.

A properly timed reply received by implantable pulse generator 10 causes transmission of a confirmation signal as shown at element 162. Element 164 causes element 166 to extinguish indicator 25 if programmer 20 receives the confirmation and to illuminate indicator 25 if programmer 20 does not receive the confirmation. Exit is via element 170.

Figure 7:
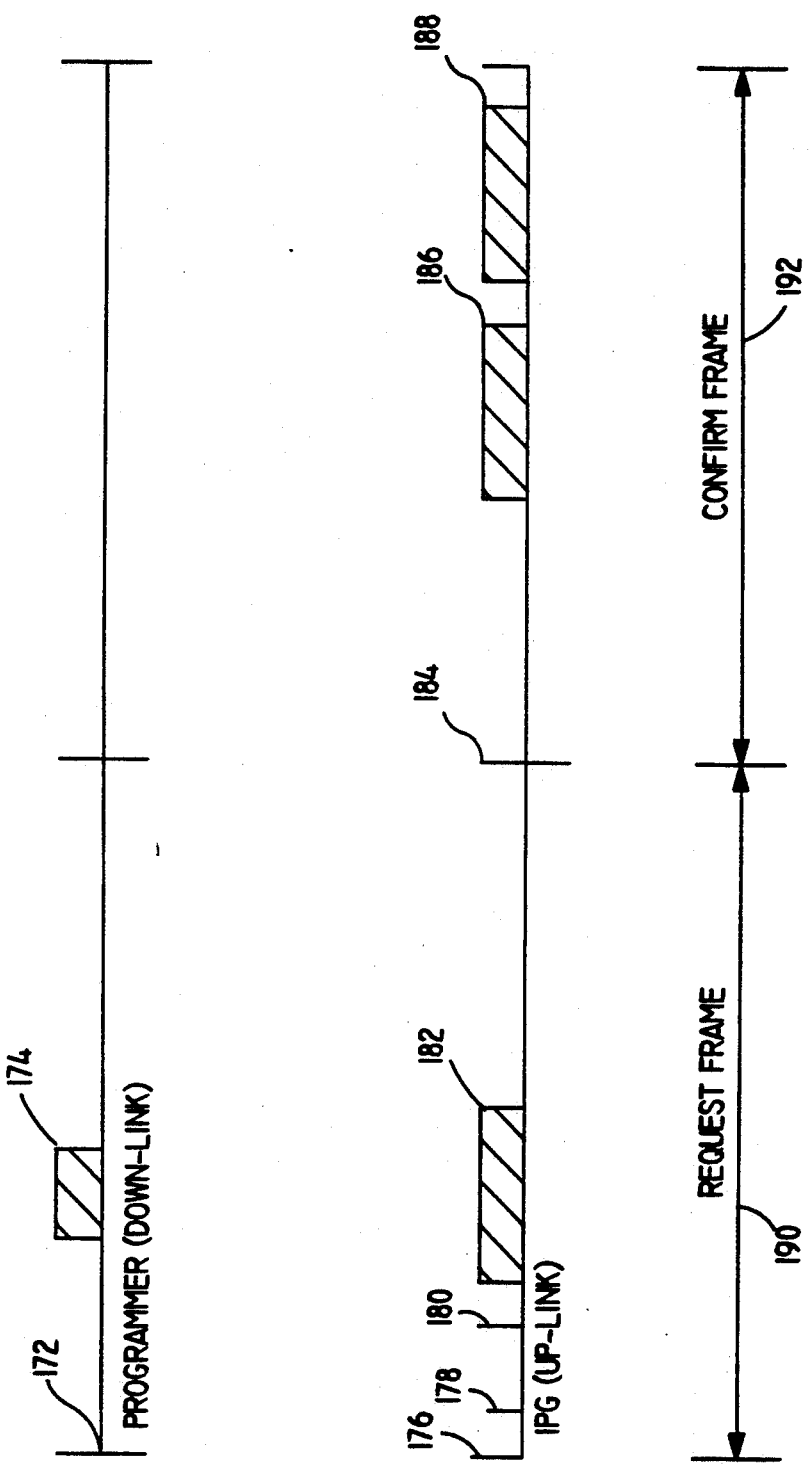
FIG. 7 is a timing diagram of a successful hand shake.

FIG. 7 is a timing diagram showing the two frame couplet associated with the hand shake procedure. The lower time line, comprising request frame 190 and confirmation frame 192 shows that the total transmission time for a successful hand shake is two frames or approximately four milliseconds.

In the preferred mode, the hand shake requestor is implantable pulse generator 10, although those of skill in the art can readily appreciate that this function could also be assigned to programmer 20. Implantable pulse generator transmits a standard frame initiation pulse at 176 and frame synchronizing pulse 178 (see also FIG. 2). The frame identification pulse 180 is chosen to uniquely identify this as a hand shake request (see also Table 1 above). Frame identification pulse 180 is placed within the frame identification range as with other frame identifiers (see also FIGS. 2 and 3).

Time window 182 is the time relative to the frame synchronizing pulse (i.e. pulse 178) during which the implantable pulse generator must receive a hand shake reply to achieve a successful hand shake. Time window 182 corresponds to the time during which the lower nibble and upper nibble of data would ordinarily be transmitted (see also FIG. 2). The frame for programmer 20 begins at point 172. If it has received and properly decoded frame identification pulse 180 as a hand shake request, it transmits hand shake reply pulse 174 as shown.

If implantable pulse generator 10 receives and properly decodes hand shake reply pulse 174 during time window 182, it transmits confirmation pulses 186 and 188 during the next succeeding frame which begins at point 184 and is defined by frame synch pulse 185 and frame identifier pulse 187. Note that the hand shake has been successful to implantable pulse generator 10 if it receives hand shake reply pulse 174 during the first frame. However, programmer 20 must wait until receipt of confirmation pulses 186 and 188 during the second frame to record a successful hand shake.

As can be readily appreciated, the use of this particular handshake technique, which uses the standard frame size and protocol, periodically ensures that synchronization between programmer 20 and implantable pulse generator 10 is maintained throughout the entire transmission. Furthermore, no data is lost following confirmation due to the need to re-synchronize.

Figure 8:
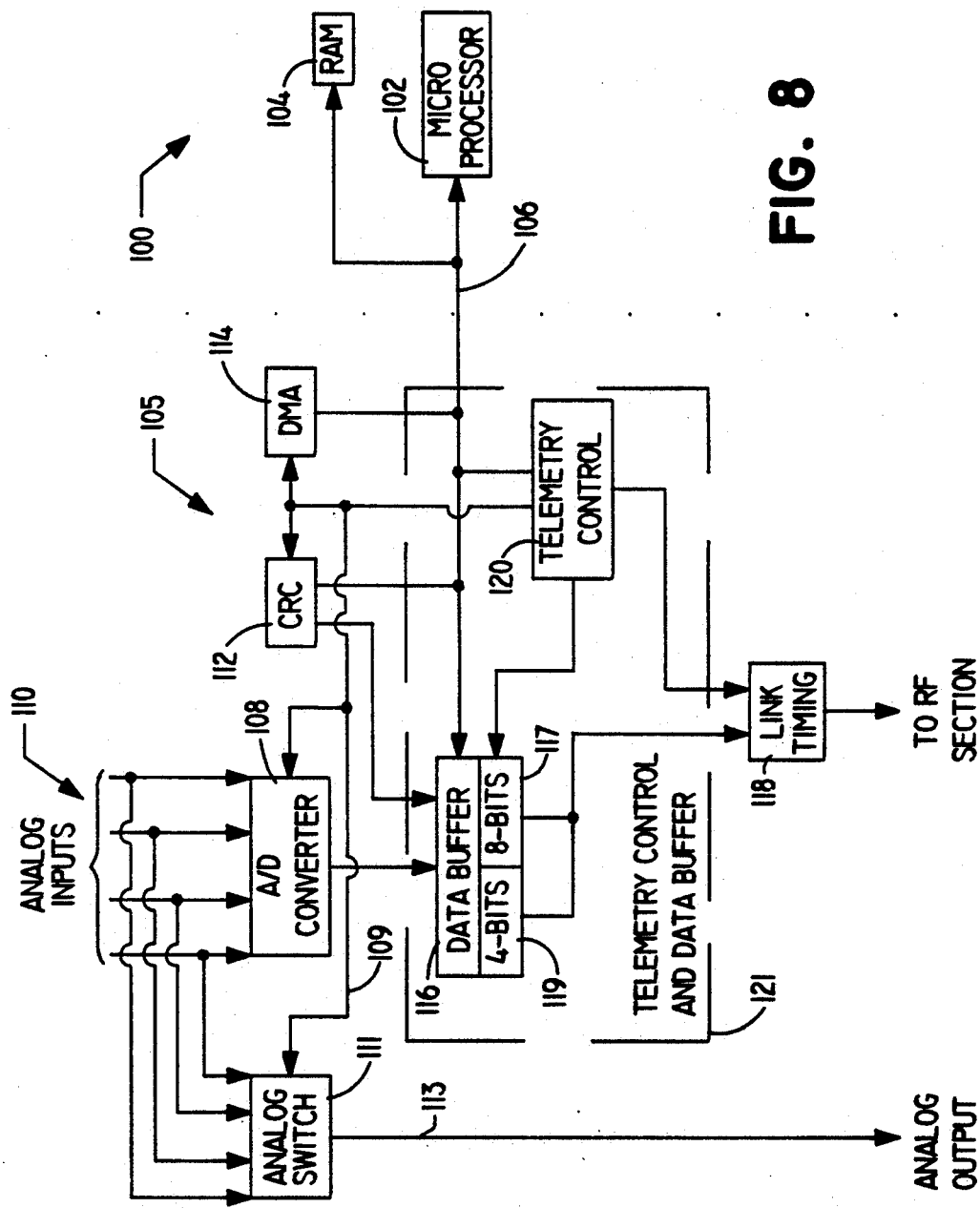
FIG. 8 is a block diagram of the transmitter base band circuitry.

FIG. 8 is a block diagram of that portion of implantable pulse generator 10 which is associated with formatting and transmission of RF up link 26. Most of the unique hardware which embodies the present invention is located on a single substrate, including custom hybridized circuitry indicated generally by arrow 105. The remainder of the hardware, which is preferably located on the same substrate, is microprocessor-based logic indicated generally by arrow 100, comprising microprocessor 102, random access memory (RAM) 104, and parallel bus 106. The function of microprocessor-based logic 100 is described in further detail below.

Hybrid circuit 105 has an analog-to-digital (A/D) converter 108 which receives a number of analog inputs 110 from a multiplexer (not shown). A/D converter 108 permits data to be transferred via RF up link 26 to be digitized as necessary. The same data may also be transmitted in analog form as discussed further below. Circuitry (CRC) for generating and analyzing the cyclic redundancy code used to forward error detect telemetry data transmitted over RF up link 26 is indicated at 112. The structure and operation of CRC 112 is also discussed in greater detail below. Because of the forward error detection technique chosen for the preferred embodiment, CRC 112 is also used for data received by implantable pulse generator 10 via down link 27.

Circuitry (DMA) for providing direct memory access to RAM 104 is indicated at 114, thus permitting multiple byte transfers without constant management by microprocessor 102.

Key hardware used to implement RF up link 26 comprises telemetry control and data buffer circuitry indicated generally within dashed lines at 121, which circuitry includes data buffer 116 and telemetry control 120, and up-link timing circuitry 118. Data buffer 116 includes storage for twelve bits of data. This storage is partitioned into a four-bit section 119 for storage of the frame identifier code, and an eight-bit section 117 for storage of the lower nibble and upper nibble of a frame. Data buffer 116 thus stores all of the variables for one complete frame. Data buffer 116 is used to stage the variables for the frame Which may be received from RAM 104, A/D converter 108, CRC 112, or elsewhere along parallel bus 106.

Telemetry control 120 consists primarily of a telemetry status register. This register stores the telemetry commands and status as loaded by microprocessor 102. The contents of the register are thus used to gate the data at the proper time of the defined protocol.

Up-link timing 118 decodes the twelve bits of data stored in data buffer 116 to produce a set of timing signals which key bursts of RF energy at the appropriate times to pulse position modulate the 175 kilohertz carrier. Up-link timing 118 also keys bursts of RF energy at the fixed positions within the frame corresponding to the frame-initiating pulse and the synchronizing pulse.

Analog inputs 110 are also presented to analog switch 111, which serves as a simple analog multiplexer. The particular analog signal to be selected for transmission on the analog channel is determined by control bus 109 which similarly selects the desired analog input for the digital channel. The analog signal selected by analog switch 111 is transferred via line 113 to the modulation hardware. The instantaneous analog value on this line will determine the instantaneous phase of the modulated bursts of carrier energy even as the output of link timing 118 determines the pulse position of those same bursts.

Figure 9:
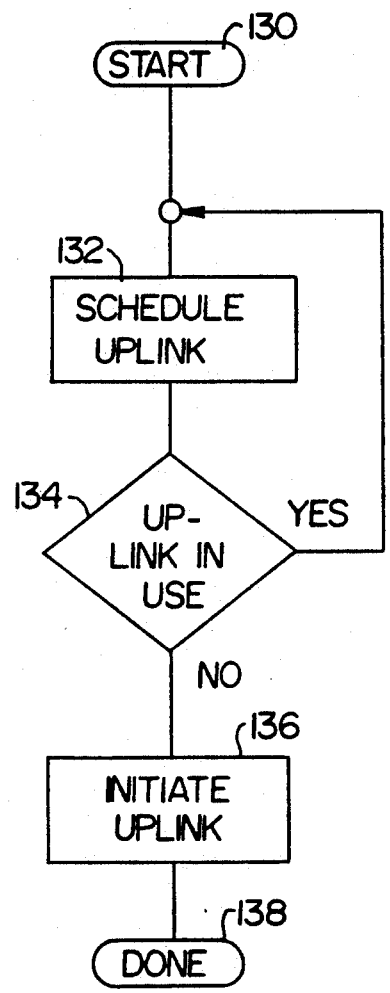
FIG. 9 is a flow chart for establishing link availability of the transmitter channel.

FIG. 9 is a basic flow chart showing the overall scheduling function of the microprocessor-based logic 100. The role is essentially one of initiation of the transfer, rather than management of each detail of the transmission. Software associated with RF up link 26 is started at element 130, usually by the initial reed switch closure (see also FIG. 5).

Element 132 schedules the requested transmission via the up-link facilities. This scheduling prioritizes up link transmission requests. Lower priority is given to continuous real time transfers, such as EGM and battery voltage, whereas higher priority is given to single occurrence transmissions of status information. Also considered is the internal timing of the cardiac pacer functions. It has been determined through experience that the most reliable results are obtained when the up-link transmission occurs between paced QRS events. Therefore, it is desirable to schedule up-link transmissions to be initiated after the conclusion of a QRS event and to be concluded before the beginning of the next QRS event.

After scheduling, element 134 determines whether an up link transmission is currently in progress. If an up link transmission is in progress, element 132 reschedules the request.

If an up link transmission is not in progress after scheduling, element 136 initiates the up link transmission by activating telemetry control 120. Exit is via element 138. While some additional management of the process is required during the transmission, a description of such further details has been omitted, since it is not believed necessary to one skilled in the art to fully understand the present invention. As to the software associated with the up link transmission, however, a source code listing of the pertinent sections of such software has been attached hereto as Appendix A, and is incorporated by reference herein.

Figure 10:
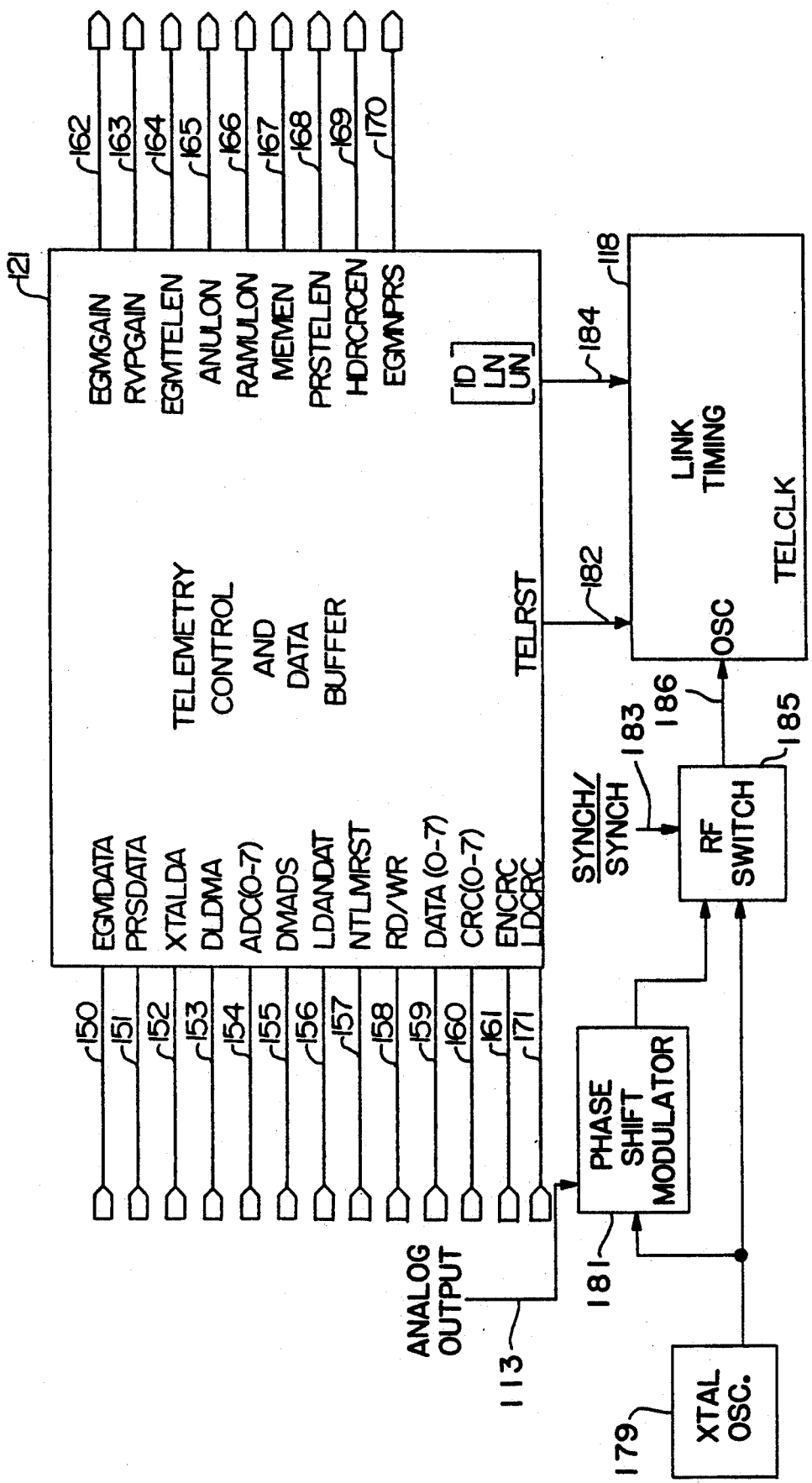
FIG. 10 is a block diagram showing the analog modulation circuitry.

FIG. 10 is a block diagram showing the modulation circuitry. It includes major data and control elements of telemetry control and data buffer 121 (which includes data buffer 116 and telemetry control 120 shown in FIG. 8), and also of up-link timing 118 which provide the digital modulation. The remaining elements shown provide the analog channel modulation.

A primary function of data buffer 116, as indicated above, is the staging of the twelve variable bits of a given frame which correspond to a four-bit frame identifier ID, and dual-nibble data comprising a four-bit lower nibble LN and a four-bit upper nibble UN. The data is received over an eight-bit, parallel bus 159 and can be from any one of several sources. Control lines EGMDATA at 150, PRSDATA at 151, DLDMA at 153, DMADS at 155, LDANDAT at 156, ENCRC at 161 and LDCRC at 171 specify the source. The output of A/D converter 108 of FIG. 8 is presented separately to data buffer 116 as an eight-bit parallel transfer to ACD(0-7) at 154 (see also FIG. 11). The output of CRC 112 is presented separately to data buffer 116 to CRC(0-15) at 160, since those devices are located on the same substrate.

Telemetry control 120 outputs a number of control signals, including EGMGAIN at 162, RVPGAIN at 163, EGMTELEN at 164, ANULON at 165, RAMULON at 166, MEMEN at 167, PRSTELEN at 168, HDRCRCEN at 169 and EGMNPRS at 170. These control outputs are used to enable and control inputs to data buffer 116. The key outputs of telemetry control and data buffer 121 are TELRST at 182, which resets up-link timing and initiates the beginning of a frame, and a parallel data transfer at 184, which transfers the frame identifier ID, lower nibble LN and upper nibble UN to up-link timing 118.

Up-link timing 118 receives the frame-initiating control signal TELRST at 182 and the parallel data transfer (ID, LN and UN) at 184. A primary function of up-link timing 118 is to key the transmission of 175 kilohertz RF energy at the proper times to indicate start of frame, frame, frame synchronization, frame identifier, lower nibble and upper nibble.

Timing for the radio frequency carrier generation is provided by the 32.768 kilohertz crystal oscillator 179. Its output is provided to phase shift modulator 181 which varies the phase in response to the analog signal present on line 113. Because the 32.768 kilohertz signal is being phase modulated, the modulation pass band of phase shift modulator 181 is about thirty times that of the effective pass band of the analog transmission channel which is limited by the number of modulated carrier bursts (i.e. three) per two millisecond frame.

RF switch 185 is a double throw switch which switches between the phase shift modulated signal received from phase shift modulator 181 and the unmodulated signal received directly from crystal oscillator 179. The switch operates in response to the state of input line 183 which indicates whether or not a frame synchronizing pulse is to transmitted. If yes, RF switch provides the unmodulated output of crystal oscillator 179 to the oscillator input of up-link timing 118 via line 186. This means that frame synchronizing bursts will have a constant phase and may therefore be utilized by the receiver as a phase standard to prevent long term phase drift.

At all times other than during the transmission of a frame synchronizing burst, RF switch 185 provides link timing 118 with a 32.768 kilohertz signal via line 186 which has been phase shift modulated with the selected analog data.

Figure 11:
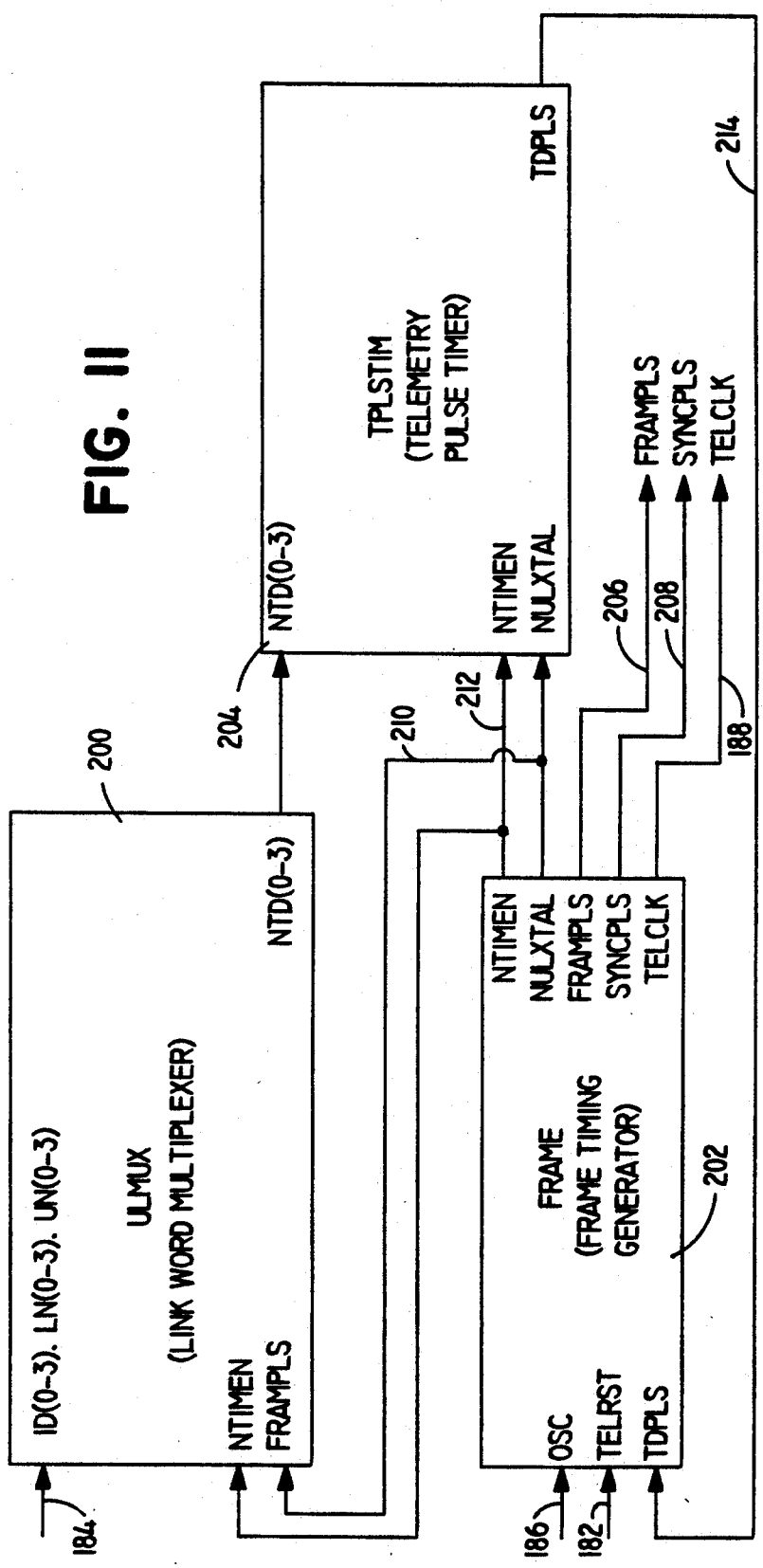
FIG. 11 is a block diagram of the digital modulation circuitry.

FIG. 11 is a block diagram of up-link timing 118. A frame timing generator 202 provides the desired timing for a frame according to clock input OSC. at 186, in a manner herein above explained. Thus, each frame is comprised of sixty-four basic clock cycles. The process is initiated by receipt of the frame-initiating control signal TELRST at 182, which enables up link when in a low state and disables up link when in a high state. The initial clock cycle of a frame contains a burst of RF energy which is keyed by control signal TELCLK at 188, which is also used to trigger the start of the data decoding by an up link word multiplexer 200.

After the proper four-bit quantity is selected (i.e., frame identifier ID first, lower nibble LN next, and upper nibble UN last), a telemetry pulse timer 204 determines the appropriate timing for a burst to be provided to frame timing generator 202, and a corresponding burst of RF energy is keyed. Each of the four-bit quantities thus results in the keying of a burst of RF energy at the appropriate time within each frame.

Figure 12:
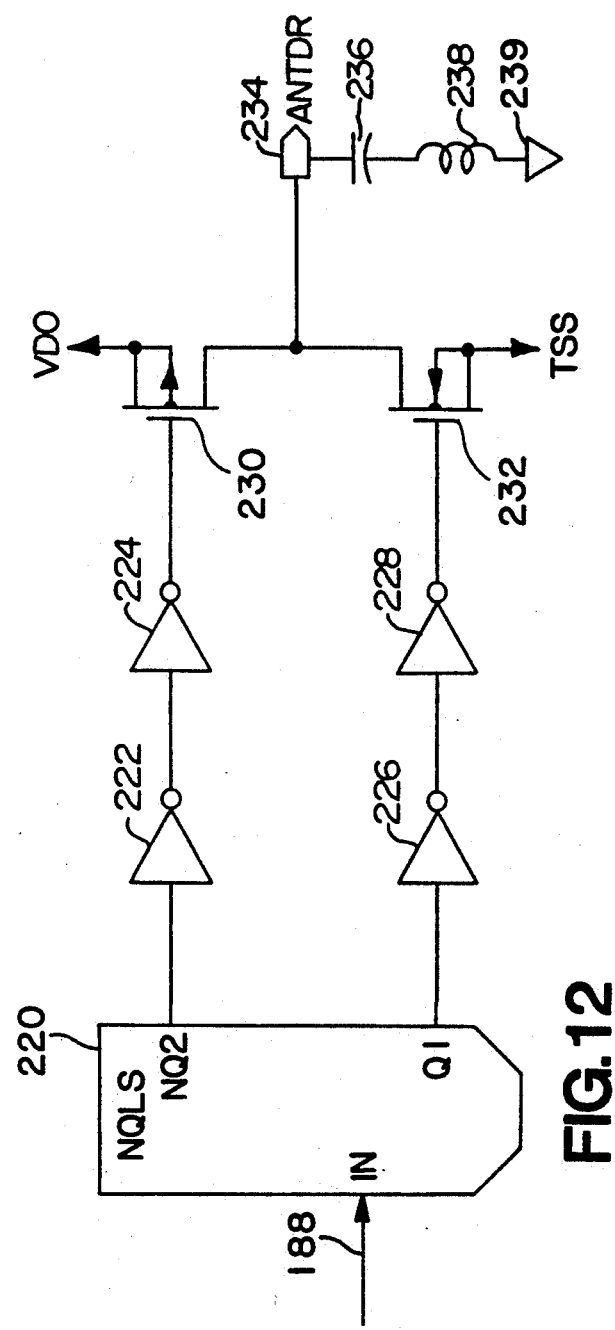
FIG. 12 is a schematic diagram of the transmitter rf circuitry.

FIG. 12 is a circuit diagram for the drive circuit for generating the RF carrier. A control signal TELCLK at 188 provides the timing information for keying the carrier. A non-overlap generator 220 functions as a delay device to save current by preventing output transistors 230 and 232 from conducting simultaneously. Every transition of control signal TELCLK at 188 causes one transition by non-overlap generator 220. Inverters 222, 224, 226 and 228 are scaled to provide efficient switching with sufficient drive to the gates of transistors 230 and 232. Transistors 230 and 232 drive the signal off of chip 105 to ANTDR at 234 to an antenna circuit. A tuned circuit of discreet components, capacitor 236 and coil 238, are located external to chip 105. Each transition thus causes this tuned circuit to resonate at 175 kilohertz, thereby generating one up link burst.

Figure 13:
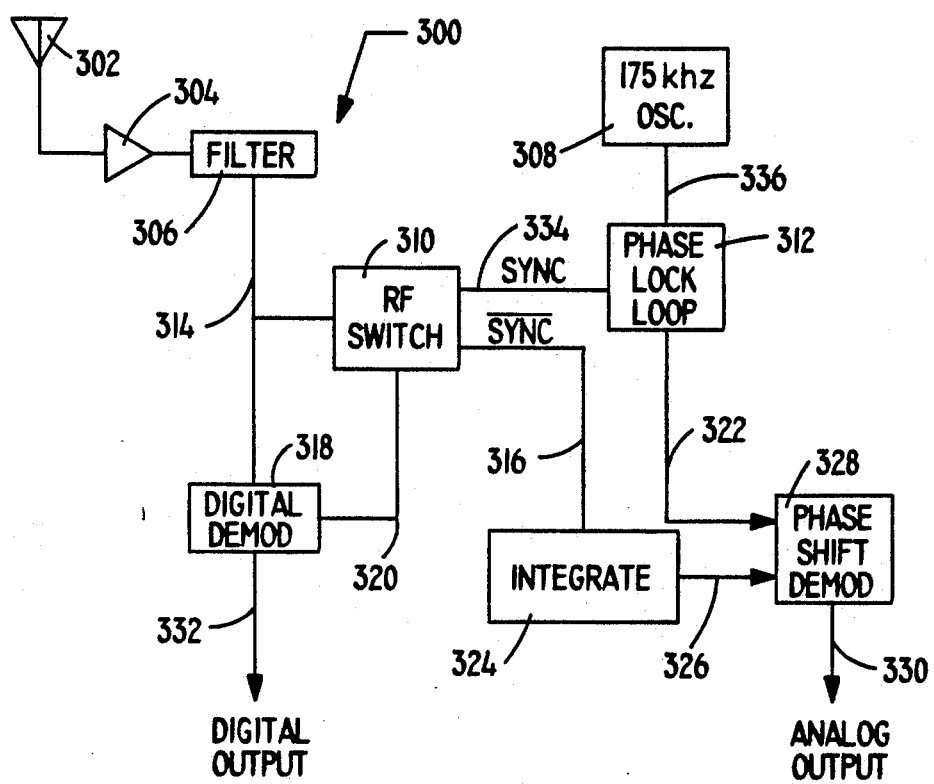
FIG. 13 is a block diagram of the receiver circuitry.

FIG. 13 is a block diagram of the receiver circuit 300 for demodulating both analog and digital channels. The radio frequency energy is received by antenna 302. For programmer 20 receiving data on up link 26 from implantable pulse generator 10, antenna 302 is the functional equivalent of the physical antenna 22 (see also FIG. 1). The radio frequency energy is amplified by rf amplifier 304 and provided to filter 306 to select the desired pass band (i.e. narrowly tuned about the 175 kilohertz carrier). The amplified and filtered radio frequency data is provided by cable 314 to digital demodulator 318 for conversion to the base band digital data stream output on cable 332.

The amplified and filtered radio frequency energy is also provided to rf switch 310 which is a simple double throw switch. Whenever a digital synchronizing pulse is present at digital demodulator 318, line 320 cause rf switch 310 to route the radio frequency energy received on cable 314 to phase lock loop 312 via cable 334. In this way the constant phase synchronizing pulses are utilized by the receiver as a phase standard for the internal 175 kilohertz oscillator 308. The phase corrected internal standard is provided to phase shift demodulator 328 via cable 322.

At all times other than when digital demodulator 318 is receiving a frame synchronizing burst, line 320 causes rf switch 310 to switch the radio frequency energy received on cable 314 to integrator 324 via cable 316. After integration, the radio frequency stream sent to phase shift demodulator 328 via cable 326 appears to be a continuous 175 kilohertz carrier which has been phase shift modulated using a relatively low frequency (i.e. less than 200 hertz) analog base band signal.

Phase shift demodulator 328 demodulates the 175 kilohertz signal received via cable 326 using the internal 175 kilohertz phase standard received via cable 322 in accordance with known techniques. The analog output on line 330 is typically an EGM or other relatively low frequency analog signal.

Figure 14:
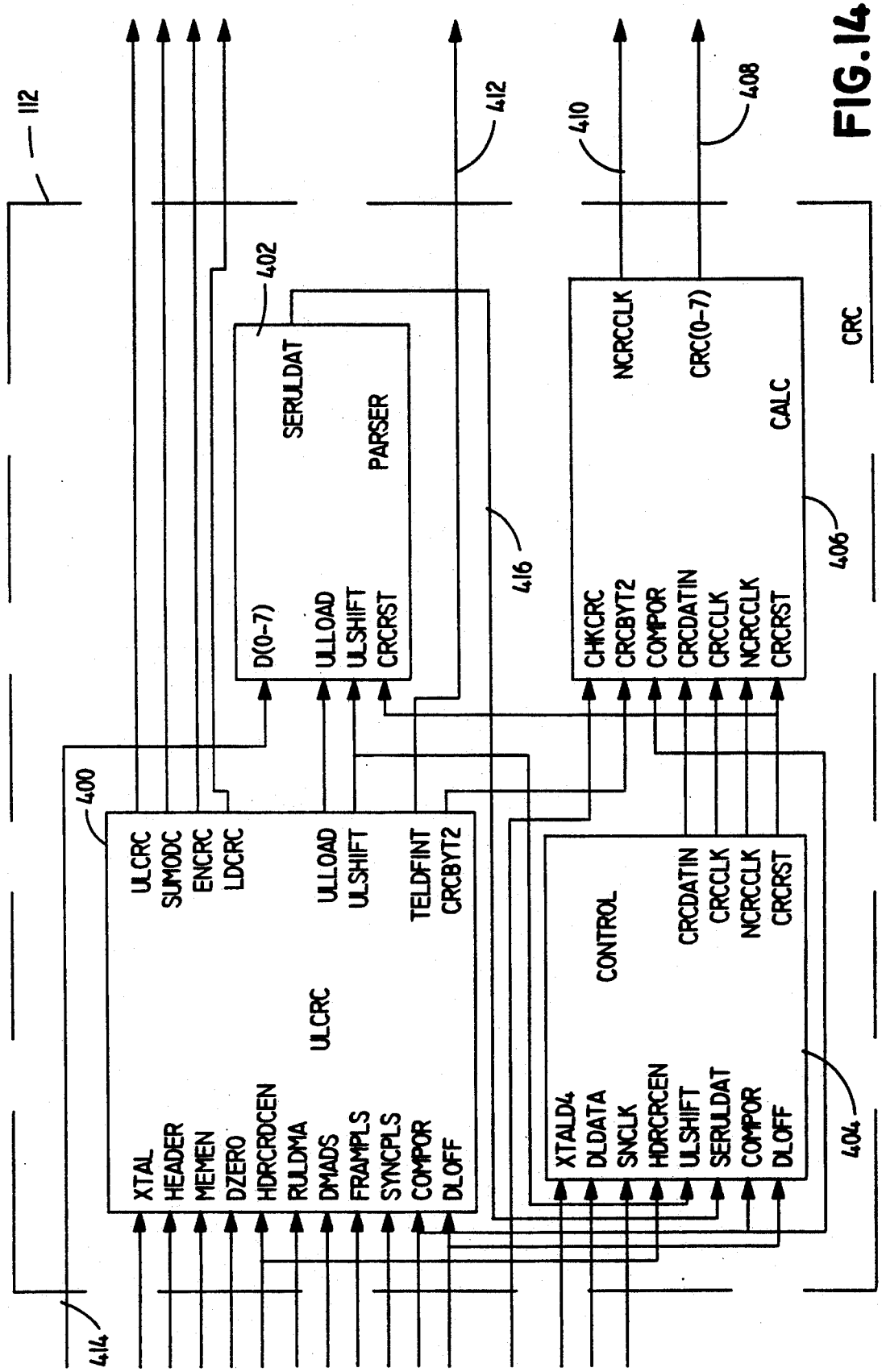
FIG. 14 is a block diagram of the cyclic redundancy code circuitry.

FIG. 14 is an overall block diagram of cyclic redundancy circuit, CRC 112. The importance of this circuit is that it provides forward error detection in a highly efficient manner using a minimum of redundant transmission band width. This becomes a significant feature for transcutaneous data links wherein total data transmission requirements are relatively large.

Forward error detection is provided by using the transmission data as coefficients of a polynomial. When this polynomial is divided (in modulo 2 arithmetic, i.e. no carry/borrow function) by a generator polynomial, the remainder is the cyclic redundancy code which is transmitted as 16 redundant bits appended to the end of the transmitted data block. The receiving device utilizes the received data, along with the cyclic redundancy code to generate a new polynomial. If division by the same generator polynomial results in a zero remainder, the transmission is assumed to have been error free. In the preferred embodiment, hardware has been used to perform these functions although those of skill in the art can appreciate that software implementation is also feasible.

CRC 112 comprises four principle circuits. The up link controller 400 provides timing signals for generation and insertion of the cyclic redundancy codes. The parser 402 serializes the incoming transmission data. Control 404 sets up the calculation process, and calculator 406 produces the actual 16 bit cyclic redundancy code, as two eight bit words. Note that except for interpretation of the result, receipt and processing of the received cyclic redundancy codes is nearly identical and is accomplished with the same hardware elements.

Figure 15:
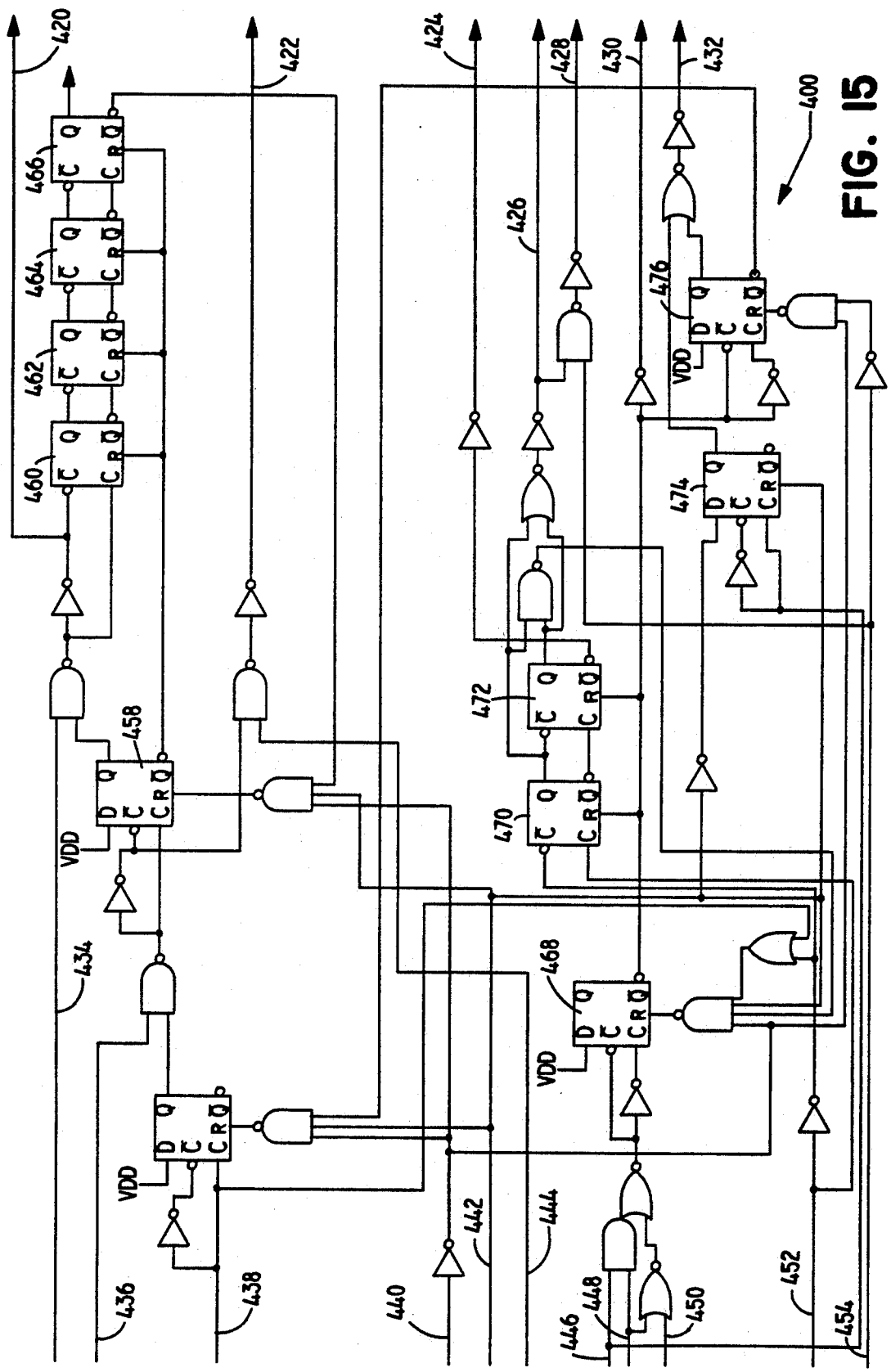
FIG. 15 is a detailed schematic diagram of the up link CRC control circuitry.

FIG. 15 is a detailed schematic diagram of the up link controller 400. The basic crystal timing standard is received via line 434. This signal times the output on line 420 of the up link shift signal held by flip flop 458, which clocks parser 402 as explained below. Flip flops 460, 462, 464, and 466 clear flip flop 458 after an appropriate delay. Flip flop 458 is clocked by the up link DMA reply (i.e. data is available on the data bus) received via line 436 and the header enable received via line 438. Resetting of these flip flops is enabled by the signal received via line 440.

After a suitable delay according to the signal received via line 442, the up link load command is place on line 422. The up link load and up link shift timing signals basically control timing of the operation of parser 402.

Control of insertion of the cyclic redundancy code into the transmitted data stream is achieved using the CRC second byte signal on line 424, the enable CRC signal on line 426, the load CRC signal on line 428, the sum signal on line 430, and the telemetry interrupt signal on line 432 (see also FIG. 14). These signals are generated as shown using DMS data synch signal on line 444, the zero signal on line 446, the memory enable signal on line 448, the header timing signal on line 450, the frame place signal on line 452, and the synch place signal on line 454 (see also FIG. 11).

Figure 16:
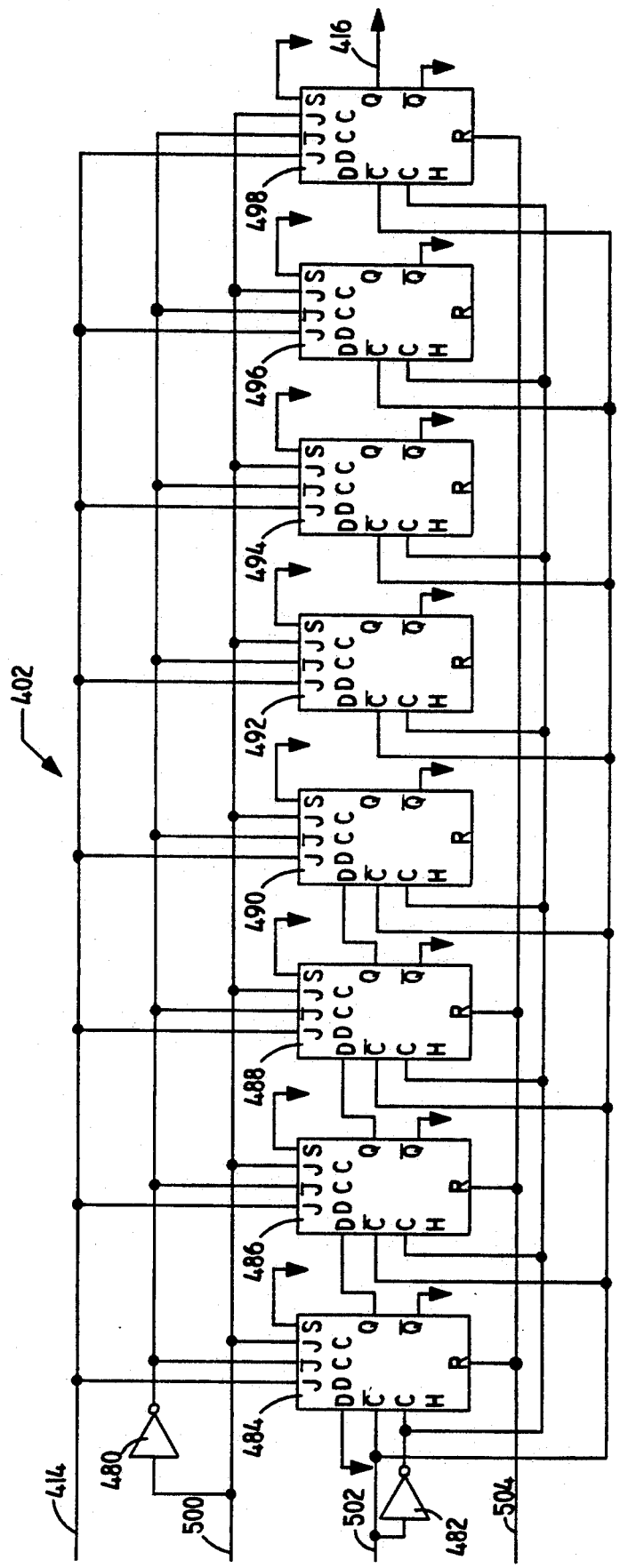
FIG. 16 is a schematic diagram of the CRC parser.

FIG. 16 is a schematic diagram of parser 402. The eight transmission data bits are received via cable 414. Each is loaded into the corresponding one of the flip flops 484, 486, 488, 490, 492, 494, 496, and 498, respectively. Loading is enabled by the up link load signal received on line 500 (see also FIG. 15) with inverter 480 providing the corresponding opposite load signal for each flip flop.

After loading of an eight bit byte into the eight bit register, the data is clocked serially from one bit position to the next to serialize the data. Clocking of this shift function which serializes the data is provided by the up link shift signal received on line 502 and invertor 482. The resulting bit stream is output on line 416.

Figure 17:
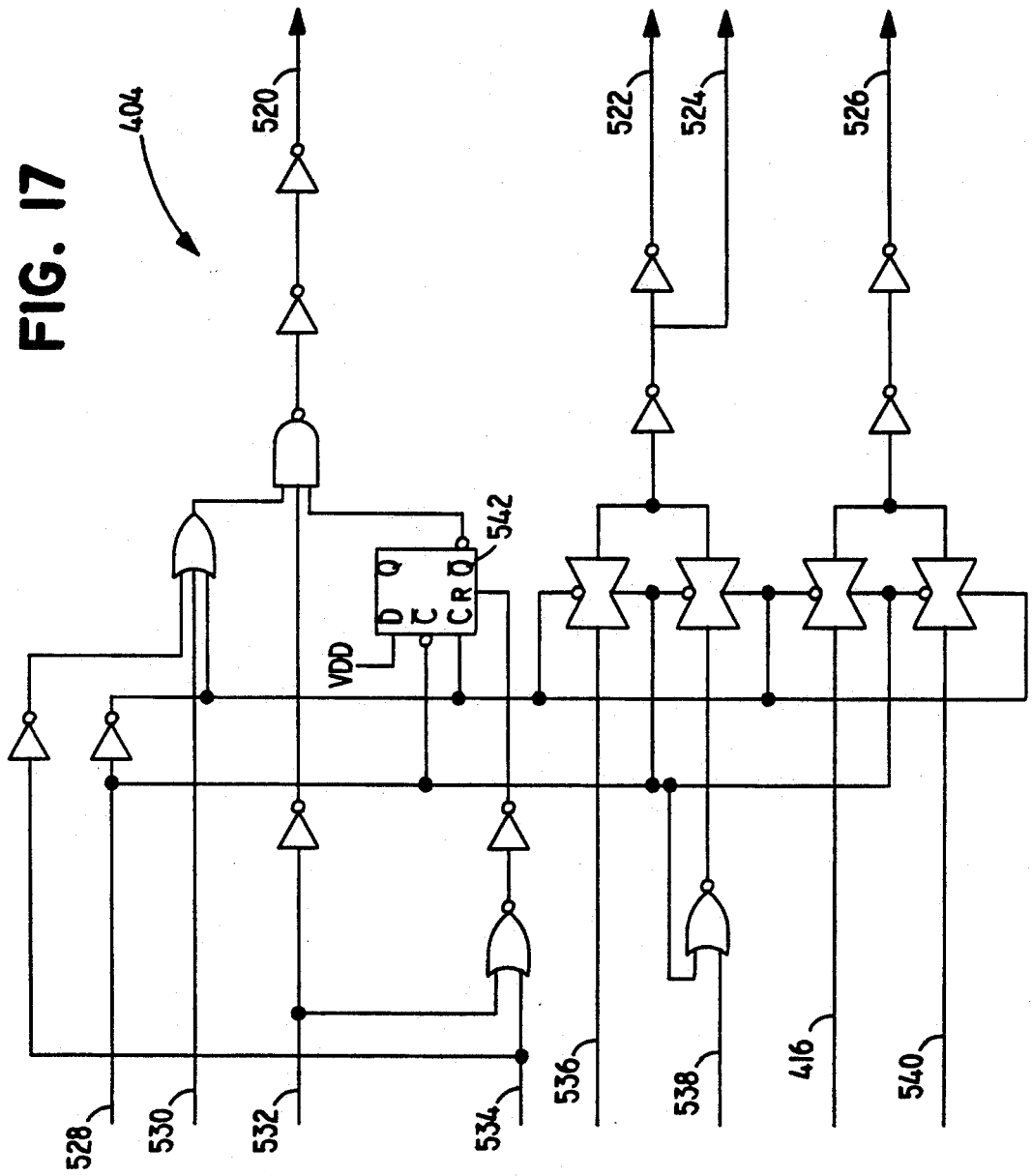
FIG. 17 is a schematic diagram of the overall CRC control circuit.

FIG. 17 is a schematic diagram of control circuit 404 which controls the CRC calculation process. The delayed clock signal received on line 528 is used to switch the CRC data in signal of line 526 alternately between the serialized up-link data received via line 416 and the down-link data received on line 540.

The outputs on lines 522 and 524 correspond to the CRC clock signal and the inverted CRC clock signal. This is produced by alternately switching between the up link shift signal received via line 536 and the synch clock signal received via line 538. This switching is accomplished at the same rate as the switching which produces the CRC data in signal. However, the latter is generally delayed by one more inverter level before being placed on line 526.

The CRC reset signal which is placed on line 520 is produced by the not output of flip flop 542 as enabled by the header enable, down-link signal or fourth delay of the crystal output. Flip flop 542 is reset by the fourth delay of the crystal output.

FIG. 17 is a detailed schematic diagram of CRC calculation circuitry 406. The outputs of this circuit are the 16 bit up-link cyclic redundancy code for transmitted data transferred via bus 408, and the corresponding down-link CRC zero check for received data, which is output on line 410.

The serialized data to be transmitted is presented to exclusive or 550 by line 526 (see also FIG. 17). This serialized bit stream is presented to flip flops 552, 554, 556, 558, 560, 562, 564, 566, 568, 570, 572, 574, 576, 578, 580, and 582. These devices provide a CRC shift register which is a single 16-bit shift register with mod 2 sum feedback. This effectively implements the modulo 2 division resulting in a 16 bit remainder. The CRC second byte signal is used to stage the two bytes of the 16-bit remainder, appending the CRC to the up-linked data stream.

The received data is clocked into the flip flops by the CRC clock signal received via line 524. Each flip flop is reset by the CRC reset signal presented on line 520. The zero check signal presented on line 410 is produced by flip flop 584, if no error is present in the received data.

Having thus described the preferred embodiments in sufficient detail as to permit those of skill in the art to practice the present invention without undue experimentation, those of skill in the art will readily appreciate other useful embodiments within the scope of the claims hereto attached.

What is claimed is:

1. In a system employing an implantable medical device and an external device which communicates with said implantable medical device via means for transmission of a stream of data and means for receiving said stream of data, and further having means coupled to said transmission means for inserting a link maintenance message into said stream of data, and means coupled to said receiving means for recognizing said link maintenance message, wherein said recognizing means is further coupled to a means for replying to said link maintenance message with a reply message, and further having means coupled to said transmission means for responding to said reply message with a confirmation message, the improvement comprising:

(a) means coupled to said transmission means for recording an inoperative link in response to failure to receive said reply message within a predetermined period of time; and (b) means coupled to said receiving means for recording an inoperative link in response to failure to receive said confirmation message within a second predetermined period of time.

2. A method of maintaining a transcutaneous information link comprising:

(a) establishing a transcutaneous information link;

(b) transferring an information link maintenance message message via said transcutaneous information link;

(c) receiving said information link maintenance message;

(d) returning an information link maintenance message reply message in response to said receiving said information link maintenance message;

(e) confirming said returned information link maintenance message reply message with a confirmation message;

(f) indicating failure to receive said confirmation message within a predetermined period of time; and (g) recording an inoperative link in response to failure to receive said reply message within a second predetermined period of time;

3. A method according to claim 2 further comprising:

(h) recording an inoperative link in response to failure to receiver said confirmation message within a third predetermined period of time.

* * * * *

UNITED STATES PATENT AND TRADEMARK OFFICE
CERTIFICATE OF CORRECTION

PATENT NO. : 5,292,343
DATED : March 8, 1994
INVENTOR(S) : Christine M. Blanchette et al.

It is certified that error appears in the above-indentified patent and that said Letters Patent is hereby corrected as shown below:

Col. 5, line 48, delete "tnr", and insert in its place --$t_{n4}$--.

Col. 11, line 22, after timing, insert --118--.

Figure 18:
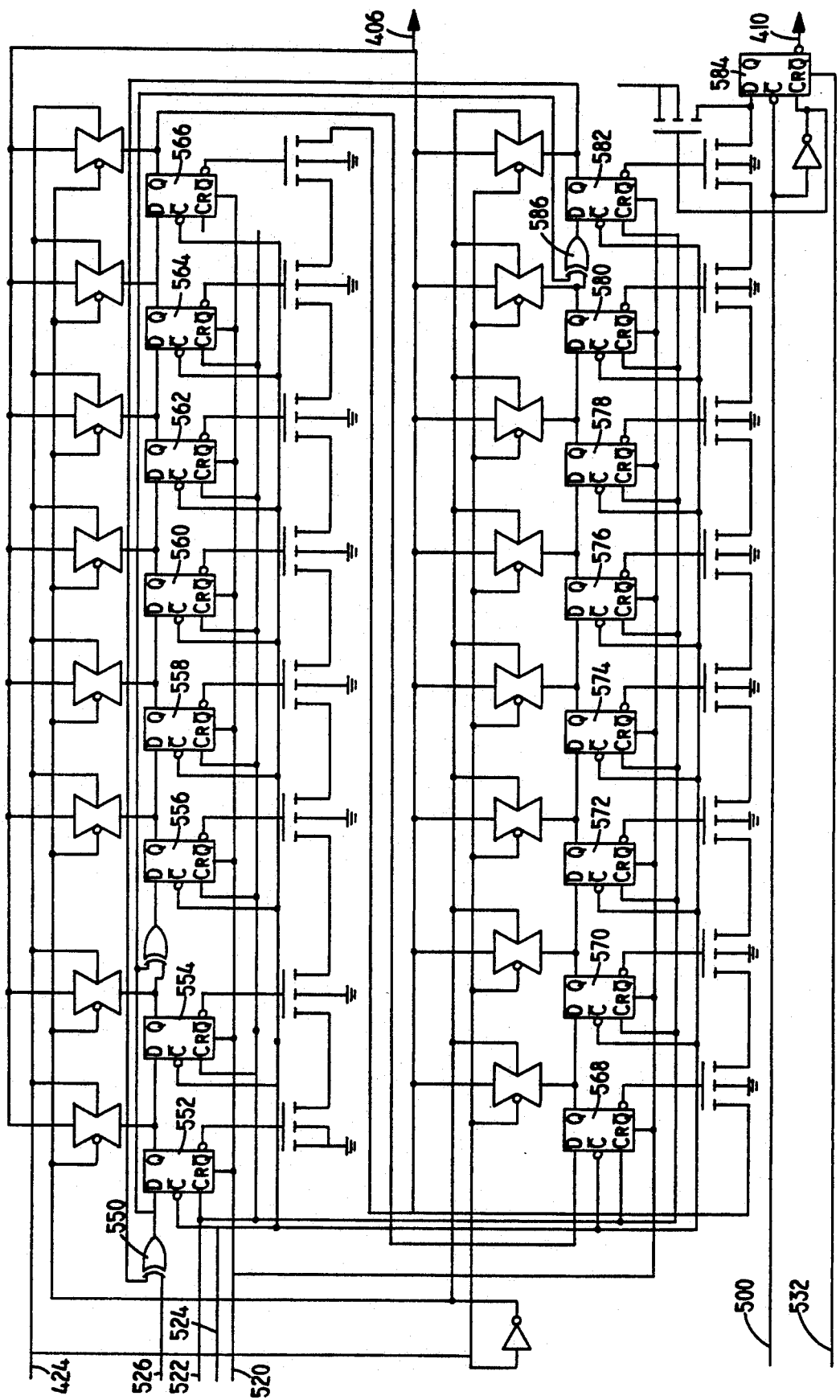
FIG. 18 is a detailed schematic diagram of the CRC calculation circuitry.

Col. 14, line 26, delete "Fig. 17", and insert in its place --Fig. 18--.

Col. 16, line 15, delete "receiver" and insert in its place --receive--.

Signed and Sealed this

Fifteenth Day of November, 1994

Attest:

BRUCE LEHMAN

*Attesting Officer*  *Commissioner of Patents and Trademarks*